United States Patent [19]

Segars

[11] 4,007,632

[45] Feb. 15, 1977

[54] APPARATUS FOR DETERMINING THE TEXTURAL QUALITIES OF FOOD

[75] Inventor: Ronald A. Segars, Hopkinton, Mass.

[73] Assignee: The United States of America as represented by the Secretary of the Army, Washington, D.C.

[22] Filed: Jan. 29, 1976

[21] Appl. No.: 653,418

[52] U.S. Cl. .................................. 73/78; 73/81; 73/101

[51] Int. Cl.² .................................. G01N 3/24

[58] Field of Search .............. 73/78, 81, 85, 101, 73/103

[56] References Cited

UNITED STATES PATENTS

| | | | |
|---|---|---|---|
| 2,209,020 | 7/1940 | Billman et al. | 73/81 |
| 2,652,718 | 9/1953 | Wiseman | 73/78 |

Primary Examiner—James J. Gill
Assistant Examiner—Anthony V. Ciarlante
Attorney, Agent, or Firm—Nathan Edelberg; Robert P. Gibson; Charles C. Rainey

[57] ABSTRACT

A punch and die test cell device for use in combination with a compression force measuring instrument in the testing of food products to determine their textural qualities, such as toughness or tenderness. Also, a method of evaluating the textural qualities of a food product by determining the value of at least one of three parameters which characterize the food. These parameters are determined by punching a cylindrically-shaped plug from a slice of the food and obtaining certain force and deformation measurements during the punching. Thereafter, calculations are made of the value of said at least one parameter and this value is compared with a standard value found to be characteristic of desirable samples of the food product.

6 Claims, 2 Drawing Figures

APPARATUS FOR DETERMINING THE TEXTURAL QUALITIES OF FOOD

The invention described herein may be manufactured, used, and licensed by or for the Government for governmental purposes without the payment to me of any royalty thereon.

BACKGROUND OF THE INVENTION

This invention relates to an improved punch and die test cell device for use in combination with a compression force measuring apparatus in the testing of food products to determine their textural qualities, such as degree of toughness, which results are found to correlate with subjective results obtained with the assistance of panels of trained or relatively expert human evaluators of food quality and a method of evaluating the textural qualities of a food product.

Much effort has been expended over many years attempting to develop an objective test for measuring food quality which will be reliable in predicting human reactions to foods, particularly from the standpoint of toughness or tenderness. Such an objective test is particularly desirable for application to meat since this is in most instances the most expensive part of a meal. Textural quality of meat is, therefore, very important to both the seller and buyer thereof, the value of meat depending more on textural qualities than on any other characteristic.

It is an object of the present invention to provide a device and a method for use in conducting objective tests of foods and for predicting the textural characteristics of foods, and more particularly for predicting their toughness or tenderness characteristics.

Other objects and advantages will become apparent from the following description of the invention.

SUMMARY OF THE INVENTION

A punch and die test cell device for use in combination with a compression force measuring instrument, such as an Instron Universal Testing Machine, in the testing of food products to determine their textural qualities, such as toughness or tenderness.

Also, a method of evaluating the textural qualities of a food product by determining the value of at least one of three parameters which characterize the food. These parameters are determined by punching a cylindrically-shaped plug from a slice of the food and obtaining certain force and deformation measurements during the punching. Thereafter, calculations are made of the value of said at least one parameter and this value is compared with a standard value found to be characteristic of desirable samples of the food product.

The cylindrically-shaped plug is punched out of a slice of the food which has a thickness between about 0.2 and 0.8 cm using a cylindrically-shaped punch having a planar end which contacts the slice of food, the plug being formed by cooperation of the punch with a circular die having a diameter of from about 0.5 to about 2.00 cm. The punch has a diameter which provides a clearance of from about 0.002 to about 0.005 cm between it and the sidewall of the die.

DESCRIPTION OF THE PREFERRED EMBODIMENT

Figure 1:
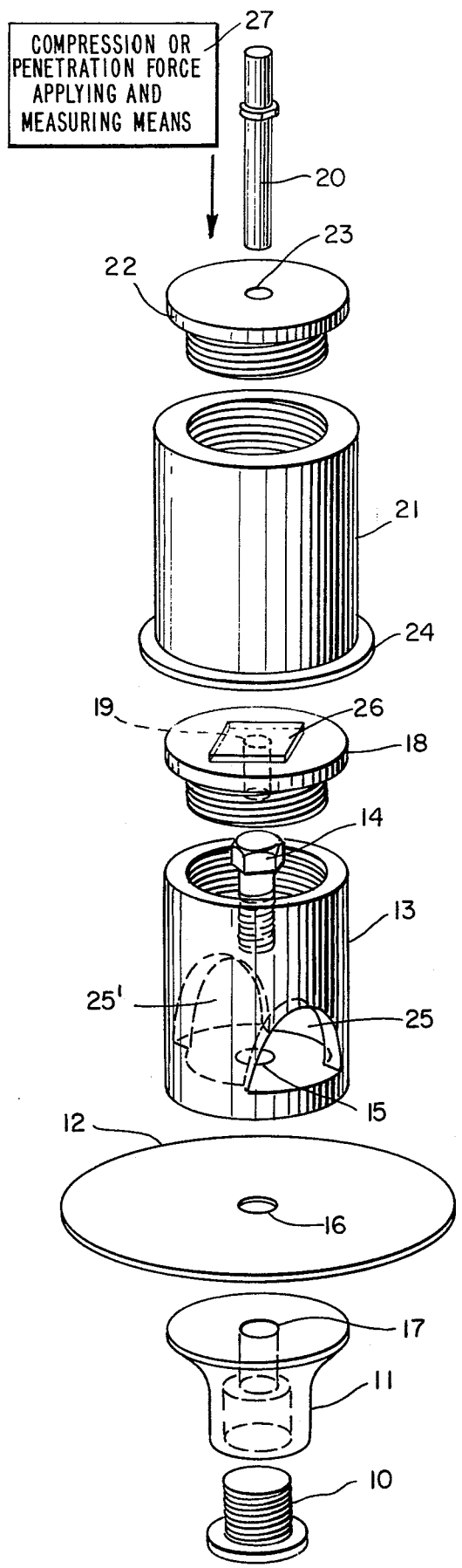

A feature of my invention is the provision of means for rapidly determining the tenderness or toughness of a slice of cooked meat or a slice of other food in an objective manner not dependent on human reactions to the biting and chewing characteristics of the cooked meat or other food. The slice of food being tested does not require clamping such as has been required in many of the apparatuses for the same or a similar purpose which have been proposed heretofore. Whenever clamping of a food sample is required, the testing process is greatly slowed.

Another feature of my invention is the adaptability of the apparatus of the invention to use in combination with almost any compression force measuring apparatus. Use of the apparatus in combination with an Instron Universal Testing Machine will be described hereinafter; but it is to be understood that with relatively minor modifications the apparatus may be used in combination with other compression force measuring equipment, e.g. various modifications of the Kramer shear press, the Warner-Bratzler shear press, the Hinnergardt et al. penetrometer (U.S. Pat. No. 3,732,727), which comprises standard elements of the Allo-Kramer shear press, and many other similar apparatuses for measuring compression forces or forces involved in penetrating a material with some type of rod or needle or other penetrating element.

The most significant feature of the apparatus of the present invention is that very high correlation coefficients are obtained between the results produced with the apparatus and subjective test results obtained in organoleptic testing of cooked meat by panels of expert technological test subjects using similar samples of cooked meat. Such correlation coefficients frequently are as high as 0.98, the maximum possible correlation coefficient being 1.00 while correlation coefficients above 0.70 relating subjective and objective data are considered high.

A further feature which adds to the broad applicability of the apparatus of the invention is that it is unnecessary to control meticulously the thickness of the samples being tested, it being only necessary to measure the actual thickness of each sample prior to or during the testing thereof. With the Instron Universal Testing Machine, measurement of sample thickness can be made part of the data output by starting the cross-head from a known distance above the shear plate and using the event marker to indicate on the recorder chart when the cross-head started down. The results are normalized by means of an equation to be given and discussed below. Thus the results obtained by several experimenters or operators are directly comparable even though they may be obtained on samples of different thicknesses. Furthermore, different sized punches may also be used while still permitting direct comparisons of results obtained by different experimenters or operators since the size of the punch is compensated for in the equations applied to the test results, as will be better understood as the apparatus and method are more fully described below.

The above-mentioned and other features and objects of the invention will become more apparent by reference to the following description of one embodiment of the invention taken in conjunction with the accompanying drawing, in which:

FIG. 1 is an exploded view in perspective of the apparatus of the invention.

Figure 2:
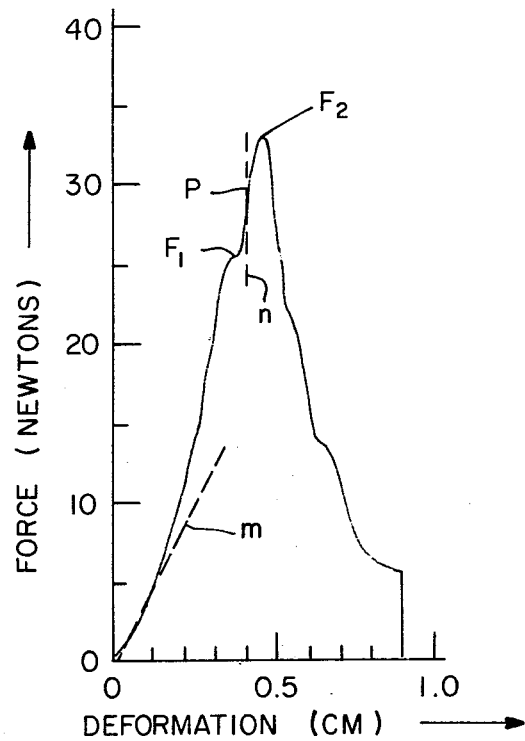

FIG. 2 shows a diagram of the force applied to a sample slice of cooked beef by a cylindrically shaped punch having a planar end at various deformations in a slice of beef, the force values as well as the extent of deformation of the sample being measured by means of an Instron Universal Testing Machine in which the apparatus of the invention is incorporated, and then normalized by means of an equation, as described hereinafter.

In the embodiment of my invention shown in FIG. 1, a load cell (not shown) of suitable capacity (usually about 50 kg for meat samples) is mounted in the compression overload carriage at the base of an Instron Universal Testing Machine (not shown). An adapter 10 attaches support base 11 of the test cell to the load cell of the Instron. Protection disk 12 and shear plate support 13 are mounted successively on and held attached to support base 11 by means of machine screw 14, which passes through hole 15 in the shear plate support and hole 16 in the protection disk into hole 17 in the support base. Shear plate 18, which supports the sample 26 in the form of a thin slice to be tested and which by means of a circularly-shaped hole 19 therein serves as a die for the purpose of punching a cylindrical plug out of the food being tested, is threadedly mounted on the shear plate support and aligned with punch 20, which is attached to the cross-head (not shown) of the Instron. The punch is a cylindrically-shaped, solid, stainless steel rod with it lower end, which contacts the sample of food, machined flat. The diameter of the punch and the diameter of die 19 in shear plate 18 are such that very close clearances are obtained. For example, when the diameter of die 19 is 1.00 cm, the diameter of punch 20 is 0.99 cm, providing a clearance of 0.005 cm between punch 20 and die 19. Frequently it is important that a sample being tested be held flat on shear plate 18 over die 19. This is accomplished by guide ring 21 in the upper end of which top plate 22 is threadedly mounted. Top plate 22 is provided with a centrally disposed hole 23 through which punch 20 passes when guide ring 21 is placed over and around shear plate support 13. The bottom surface of top plate 22 rests upon the top surface of the sample 26 being tested. Guide ring 21 is provided with a flanged base 24 which supports weight rings (not shown) if needed to increase the force bearing down on the top surface of the sample 26 to maintain the sample flat and to prevent or reduce slipping thereof during testing. Shear plate support 13 is provided with windows 25 and 25' through which punched out plugs of food sample may be removed from the interior of shear plate support 13 without dismantling the apparatus.

Evaluation of the textural characteristics of cooked beef muscle is carried out with the apparatus of the invention in the following manner:

For the purpose of comparing various cooked muscles of beef with respect to tenderness or toughness thereof three different muscles, namely the psoas major, the semitendinosus, and the biceps femoris muscles are excised intact from each of a U.S. Choice and U.S. Commercial grade animal and trimmed free of all excess fat. The biceps femoris muscles are cut in half. A copper-constantan thermocouple is inserted into the approximate center of each muscle, or half muscle in the case of the biceps femoris muscles. Each muscle is then enclosed in a separate polyethylene bag; and the bags are tied at the top and suspended in a steam jacketed kettle filled with water, the tops of the bags being kept above the water line while all parts of the muscles are submerged. The three U.S. Choice grade muscles are cooked simultaneously and the three U.S. Commercial grade muscles are also cooked simultaneously. The water temperature in the kettle is maintained between 63° and 65° C. throughout the cooking of both sets of muscles. The cooking is considered complete when the internal temperature of a given muscle recorded using the thermocouple embedded in that particular muscle reaches 63° C. This cooking procedure results in a very uniform cooking of all of the muscles. The time required to cook the muscles varies from about 2.25 hours for the U.S. Choice psoas major muscle to 6.5 hours for the halved U.S. Choice biceps femoris muscle. The cooked muscles are refrigerated overnight before cutting them into test samples. Slices approximately 1.27 cm thick are prepared on a commercial meat slicer with the muscle fibers substantially perpendicular to the cut surfaces of the slices for technological panel testing; and slices approximately 0.4 cm thick are prepared also on a commercial meat slicer with the muscle fibers, as in the case of samples for technological panel testing, substantially perpendicular to the cut surfaces of the slices, for testing on the apparatus of the invention. Out of these 0.4 cm thick slices, test samples 26 are prepared by cutting squares approximately 4.0 cm on each side from the slices prepared from the cooked muscles. For technological panel testing, samples approximately 3.2 cm square are prepared from the 1.27 cm thick slices and equilibrated to room temperature before serving these samples to the panel members. The samples for instrument testing are equilibrated to 20° C. and kept in covered trays prior to testing thereof to reduce moisture loss from the samples prior to testing.

In conducting textural quality testing of samples of beef slices prepared as above-described, shear plates having circularly-shaped holes or dies therein having diameters of 0.5, 1.00, and 2.00 cm are used, the 1.00 cm diameter being selected as the preferred hole size. For testing using shear plates having circularly-shaped holes or dies therein of these diameters the cylindrically-shaped food penetrating punches have diameters of approximately 0.496, 0.99, and 1.994 cm, respectively, providing clearances between the food penetrating punches and the walls bounding the circularly-shaped holes or dies in the shear plates of 0.002, 0.005, and 0.003 cm, respectively.

It has been found to be generally desirable to test 10 replicates for each muscle in order to produce test results with the apparatus which will correlate well with sensory testing by a technological panel. Each sample 26, prepared as described above and equilibrated to 20° C., is placed in turn on the shear plate 18 so that the sample 26 overlaps the circularly-shaped hole or die 19 in the shear plate 18 substantially equally from approximately the midpoints of each pair of opposite sides of the four sides of the sample 26. A compression or penetration force applying and measuring means 27, such as an Instron cross-head together with its force measuring and recording means, and punch 20 attached thereto are set in motion in the direction indicated by the arrow shown in FIG. 1 at a velocity of about 5 cm per minute. Upon contacting of the sample of beef muscle by the lower planar-faced end of the punch, measuring and recording of a curve such as that shown in FIG. 2 begins and proceeds until the force is reduced to zero at about 0.9 cm from the origin. The Instron is set to reverse the direction of the cross-head when the lower planar-faced end of the punch has travelled to about 0.5 cm below the upper surface of the shear plate.

Thus, in the case of 0.4 cm thick slices of beef, the deformation is measured and recorded from about 0.4 cm above the upper surface of the shear plate to 0.5 cm below the upper surface of the shear plate, as is seen in the graph in FIG. 2.

FIG. 2 shows a typical force-deformation curve obtained with the apparatus of the invention applied as described above to a sample slice of beef muscle. Beginning at the origin the force, F, is zero. As soon as the punch begins to meet with resistance from the beef muscle, the force begins to rise and continues rising in accordance with the curve plotted by the recorder as the punch deforms and penetrates into the sample slice of beef muscle. The first short portion of the curve is relatively inelastic up to from about 0.02 to about 0.03 cm deformation. Then comes a relatively straight line (elastic portion) of the curve which is extrapolated in a broken line in FIG. 2, the slope of which is designated by reference letter $m$, the slope being employed in a computation of the stiffness S of the sample, which will be more particularly discussed hereinafter. This substantially straight line portion of the curve is produced from about 0.02 to 0.03 cm to about 0.14 to 0.15 cm deformation. Then the curve rises more precipitously over small increments of deformation of the beef muscle until it reaches a plateau, designated by reference letter $F_1$, from which a first important parameter of the beef sample, first punch shear stress, $\gamma_1$, is calculated employing the equation (1):

$$\gamma = \frac{F_t}{\pi d T_o} \tag{1}$$

in which $\gamma$ represents punch shear stress, $F_t$ represents the tangential force exerted by the punch, $d$ represents the diameter of the punch, and $T_o$ represents the thickness of the sample. The denominator, $\pi d T_o$, represents the area, $A_t$, of the cylindrical element over which the tangential force $F_t$ is initially distributed in punching a cylindrically-shaped plug of beef muscle out of a sample slice of beef muscle.

Equation (1) is employed in normalizing values obtained with the apparatus of the invention. It serves to eliminate the effects of thickness of the sample and diameter of the punch from the results so that results obtained by different operators using samples of different thicknesses, provided the actual thickness is known for use in equation (1), and apparatus employing punches of the type employed in the invention having different diameters may be directly compared using samples having thicknesses from about 0.2 to about 0.8 cm.

Continuing along the curve shown in FIG. 2, the plateau, from which $\gamma_1$ is calculated, occurs when the punch is still about 0.01 to about 0.04 cm above the surface of the shear plate. It is theorized that this plateau results from or during the initial yielding of the sample under a combination of tensile and shearing deformation. Following completion of this plateau portion of the force-deformation curve, the curve takes another precipitous upward path to a peak force value, $F_2$. It is believed that the peak force, $F_2$, occurs when the last of the connective tissue in the sample of beef muscle ruptures. This usually occurs when the flat face of the punch is about 0.04 cm below the upper surface of the shear plate. It is theorized that the portion of the curve between the plateau at $F_1$ and the peak at $F_2$ represents the result of the action of the punch and the wall of the shear plate bounding the circularly-shaped hole or die 19 in the shear plate 18 on the beef muscle connective tissue being drawn into the clearance between the punch and the bounding wall of the hole or die 19 and being stretched and sheared by the punch as it progresses from the level of about 0.01 cm above the surface of the shear plate 18 (about the end of the plateau portion of the curve) to about 0.04 cm below the upper surface of the shear plate 18 (corresponding to the peak point $F_2$). The broken line, designated by the reference letter $n$ represents the deformation of the sample when the planar-faced end of the punch is substantially level with the upper surface of the shear plate 18. Reference letter P represents the force being applied at this level which is approximately midway between the plateau force, $F_1$, and the peak force $F_2$. After passing through the peak $F_2$, the force-deformation curve drops off rapidly until the deformation is stopped at 0.5 cm below the upper surface of the shear plate. The portion of the curve beyond the peak force $F_2$ is not considered particularly important other than in establishing the peak force $F_2$ in the curve. $F_2$ is employed in equation (1) to calculate $\gamma_2$, the punch shear stress at the maximum in the force-deformation curve for a given sample. $\gamma_2$ is a second important parameter characterizing the beef muscle, or other food product (in the event that some other food product is being tested with respect to tenderness or toughness).

A third parameter or characteristic of the beef muscle, or other food product, is the stiffness S, which has been alluded to above. This is calculated from data obtained from the curve obtained with the apparatus and recorded as in FIG. 2 in accordance with the following equation (2):

$$S = \frac{m}{\pi d} \tag{2}$$

in which S represents stiffness of the meat or other food and is the force per unit cylindrical area swept out by the perimeter of the punch as it moves through the sample. This area is determined for ideal conditions using the following equation (3):

$$A = \pi d v_p t \tag{3}$$

in which $A$ is the cylindrical area swept out by the perimeter of the punch, $v_p$ is the velocity of the punch, $d$ is the diameter of the punch, and $t$ is the time elapsed since deformation started. As previously stated, $m$ is the slope of the first linear portion of the force-deformation curve, which is porportional to a force-time curve since the punch travels downwardly as indicated by the arrow in FIG. 1 at a controlled velocity. As stated previously, the Instron cross-head travels downwardly at a velocity of 5 cm per minute; therefore, the punch deforms the beef muscle sample at the same velocity. Hence, approximately 0.18 minutes pass while the sample of beef muscle is being subjected to the penetrating action of the punch from the first contact of the flat face of the punch with the sample slice of meat until the force has dropped sufficiently to end the test, whereupon the Instron automatically reverses and returns the punch to a position sufficiently above the shear plate to permit the removal of the tested sample slice from the upper surface of the shear plate 18 and the placing of a new sample thereon for testing.

As has been pointed out above, the results obtained with the apparatus of the invention have been compared with subjective results obtained by employing panels of trained human evaluators of food quality. This was done by carrying out sensory evaluation of cooked beef muscles which had been tested with the apparatus of the invention as described above. In these sensory evaluations, seventeen food technologists who were experienced in the sensory testing of foods constituted the panel of evaluators. Three different texture attributes were subjectively evaluated for each of the six different muscles by an accepted magnitude estimation method. These three attributes and their definitions are:

1. Difficulty of cutting: Using the teeth on the first or second chews, the degree of difficulty experienced in cutting the sample into two pieces.
2. Chewiness: The overall effort required to chew the meat on the first and subsequent chews.
3. Residue: The amount of unchewable material remaining in the mouth just before swallowing after the normal effort to chew the sample up.

The following guidelines were employed by the panelists in assigning magnitude estimates for the three different attributes in the six different muscle samples: The more difficult the sample was to sever in the mouth, or the more chewy the sample, or the greater the amount of residue left, the higher the number assigned for a given attribute of a given sample. Conversely, the easier it was to sever the sample in the mouth, or the less chewy the sample, or the less residue left, the lower the number assigned for a given attribute of a given sample. For example, if the number 30 was assigned to the first sample and a subsequent sample seemed to have about two-thirds as much of the attribute, the number 20 would be assigned to that sample. On the other hand, if a subsequent sample appeared to have about one and one-half times the attribute of the first sample, the number 45 would be assigned to the subsequent sample.

One sample from each of the six muscles was presented to each member of the panel, the samples being selected in a random fashion. The panelists were asked to evaluate the samples in a given order with respect to each of the three attributes by assigning positive numbers, including decimal values, but not zero.

Correlation coefficients for the various paired combinations of the averaged magnitude estimates for the three attributes evaluated by the panel and the three parameters obtained with the apparatus of the invention were calculated and are shown in Table 1. All of these correlation coefficients are above 0.9 and are considered excellent.

TABLE 1

Correlation coefficients between the means of sensory attributes and instrumental measurements.

|  | Chewiness | Residue | $\gamma_1$ | $\gamma_2$ | S |
| --- | --- | --- | --- | --- | --- |
| Difficulty of Cutting | 0.996 | 0.992 | 0.969 | 0.981 | 0.919 |
| Chewiness |  | .994 | .979 | .973 | .932 |
| Residue |  |  | .965 | .969 | .919 |
| $\gamma_1$ |  |  |  | .975 | .982 |
| $\gamma_2$ |  |  |  |  | .945 |

Since the correlation of the objective tests applied to the beef muscle samples using the apparatus of the invention with subjective tests carried out with a technological panel of food quality evaluators has proven to be excellent (correlation coefficients above 0.9), the tenderness or toughness characteristics of cooked beef may be quickly and reliably ascertained by applying the process of the invention to slices of cooked beef as described above. In general the higher the values obtained for the parameters, $\gamma_1$, $\gamma_2$, and S, the tougher the meat, and conversely the lower the values of these parameters, the more tender the meat. With such high correlation coefficients versus organoleptic tests being available as a result of the apparatus and method of the present invention, it is now possible to dispense with very time-consuming subjective testing of meats as well as many other food products with respect to toughness or tenderness of such food products. For beef it has been found that $\gamma_2$ values correlate better with subjective evaluations of tenderness or toughness than either $\gamma_1$ values or S values.

Standards can be established for desirable magnitudes of the parameters $\gamma_2$, $\gamma_1$, or S as obtained for a given type of food product or as taken from a selected portion of an animal or other source of food. Thus the $\gamma_2$ value obtained for a given test sample may be compared with a standard established by a study of various representative or desirable examples of that type of food product to determine its suitability or desirability with respect to toughness or tenderness.

It should be apparent from the foregoing description of the apparatus of the invention and the manner in which it is used in the evaluation of the textural qualities of food products that I have provided the bases for a significant improvement in objective experimental studies of texture and in the correlation of such objective studies with subjective evaluations of various textural qualities of food products of various types. The apparatus has been found to be particularly useful and effective in connection with meat products. It has also been found to be quite effective in connection with textural studies of certain vegetable products, such as tomatoes. If used commercially, the apparatus should prove very useful for predicting consumer perception of tenderness of certain foods, especially meats, with a high degree of reliability. The invention also shows considerable promise in the more efficient utilization of certain muscles, such as the psoas major muscles from relatively inexpensive grades of beef animals, such as U.S. Commercial grade animals in which in at least certain cases the psoas major muscles have been shown to be as tender as the biceps femoris and the semi-tendinosus muscles from U.S. Choice grade animals.

I wish it to be understood that I do not desire to be limited to the exact details described, for obvious modifications will occur to a person skilled in the art.

I claim:

1. In an apparatus for evaluating the textural characteristics of a food product of the type comprising a rod-like food penetrating punch means and means for applying a compression or penetration force to said food product through said punch means and for measuring said force, said punch means being detachably attached to the compression or penetration force applying component of said means for applying a compression or penetration force and for measuring said force, the improvement comprising means for supporting a slice of said food product in a substantially horizontal plane substantially perpendicular to the central axis of said punch means, said food slice supporting means comprising a shear plate, a hollow cylindrically-shaped shear plate support, a solid circularly-shaped protection disk on which said shear plate support rests and to which said shear plate support is detachably attached, a support base means for supporting said protection disk in a substantially horizontal plane and an adapter means conformed to mate with said support base means so as to maintain said support base means, said protection disk, said shear plate support, and said shear plate properly oriented relative to said punch means, said adapter means being detachably attachable to a lower vertically movable or stationary element of said compression or penetration force applying and measuring means, said shear plate being detachably attachable to the upper portion of said shear plate support and having a circularly-shaped die passing vertically through said shear plate with its central vertical axis coinciding with the central vertical axis of said shear plate, said circularly-shaped die having a diameter less than but not more than about 0.01 cm less than the diameter of said punch means, said punch means having a substantially planar face on its lower end, said punch means and said shear plate being oriented so as to cooperate whereby said punch means enters into said circularly-shaped die while completing the punching of a plug from a slice of said food product being supported by said shear plate, the force measuring component of said means for applying a compression or penetration force and for measuring said force measuring and recording the force being applied by said punch means to said food product as said punch means punches said plug from said slice of food product.

2. Apparatus according to claim 1, wherein said circularly-shaped die has a diameter of from about 0.5 to about 2.00 cm and said punch has a diameter such that the clearance between said punch and the sidewall of said die is from about 0.002 to about 0.005 cm.

3. Apparatus according to claim 1, wherein a further improvement comprises a hollow cylindrically-shaped guide ring and a top plate adapted to mate with said guide ring in the upper portion thereof, said guide ring fitting snugly over said shear plate and shear plate support so that when said guide ring and said top plate are mated and placed in operating position over said shear plate and shear plate support said top plate bears down on a food slice located in an operating position on said shear plate with sufficient force to maintain said food slice substantially flat against the upper surface of said shear plate during said evaluation, said top plate having a circularly-shaped die passing vertically therethrough with its central vertical axis coinciding with the central vertical axis of said shear plate and having a diameter equal to or greater than the diameter of said circularly-shaped die in said shear plate, said hole in said top plate and said die in said shear plate being located so that said punch passes through both said hole in said top plate and said die in said shear plate during the punching of a plug from said slice of food product in the evaluation of the textural characteristics of said food product.

4. Apparatus according to claim 2, wherein said guide ring has a flanged bottom edge for supporting a plurality of ring weight means, said ring weight means fitting over said guide ring and applying additional force distributed substantially uniformly by said top plate over the upper surface of said food slice during the evaluation of the textural characteristics of said food product.

5. Apparatus according to claim 1, wherein said shear plate support is provided with at least one window passing through a portion of the sidewall of said shear plate support, said window providing access to the interior space within said shear plate support for removal of plugs of food product punched out of food slices during the evaluation of the textural characteristics of said food product.

6. Method of evaluating the textural qualities of a food product which comprises the steps of:
a. punching a cylindrically-shaped plug out of a slice of said food product of a thickness between about 0.2 and about 0.8 cm by means of a cylindrically-shaped punch having a planar end which contacts said food product cooperating with a circularly-shaped die having a diameter of from about 0.5 to about 2.00 cm and providing a clearance between said punch and the sidewall of said die of from about 0.002 to about 0.005 cm, said punch moving at a substantially constant velocity as it punches said plug from said slice of food product,
b. measuring and simultaneously recording on a chart the force required to punch said plug from said slice of food product, said force being continuously measured and recorded as a curve on orthogonal coordinates of force and deformation,
c. determining from said curve the slope of the elastic portion thereof,
d. calculating the stiffness S parameter of said slice of food product with the assistance of equation (2),
e. determining from said curve the value of force $F_1$,
f. calculating the punch shear stress $\gamma_1$ parameter for said slice of food product with the assistance of equation (1),
g. determining from said curve the value of force $F_2$, and
h. calculating the punch shear stress $\gamma_2$ parameter for said slice of food product with the assistance of equation (1), wherey said $\gamma_1$, $\gamma_2$, and S values constitute reliable physical measurements of the tenderness or toughness of said food product.

* * * * *